(12) United States Patent
Maki

(10) Patent No.: US 7,687,258 B1
(45) Date of Patent: Mar. 30, 2010

(54) DIRECT ELECTRIC BIOLOGICAL AGENT DETECTOR

(76) Inventor: Wusi C. Maki, 1080 W. Harbor View Dr., Coeur d'Alene, ID (US) 83814

(*) Notice: Subject to any disclaimer, the term of this patent is extended or adjusted under 35 U.S.C. 154(b) by 0 days.

(21) Appl. No.: 10/442,819

(22) Filed: May 20, 2003

Related U.S. Application Data

(60) Provisional application No. 60/382,401, filed on May 20, 2002.

(51) Int. Cl.
*C12M 1/36* (2006.01)

(52) U.S. Cl. ............... 435/287.2; 435/283.1; 435/287.1; 429/90; 429/92; 436/150; 436/518; 436/525

(58) Field of Classification Search ............ 435/4–7.95; 436/518, 806, 825; 424/83; 257/40, 52, 257/642; 525/54.1–31
See application file for complete search history.

(56) References Cited

U.S. PATENT DOCUMENTS

| | | | | |
|---|---|---|---|---|
| 4,020,830 A * | 5/1977 | Johnson et al. | ............. | 600/348 |
| 4,322,680 A * | 3/1982 | Janata et al. | ............. | 324/71.2 |
| 4,490,216 A * | 12/1984 | McConnell | ............. | 205/777.5 |
| 4,585,652 A * | 4/1986 | Miller et al. | ............. | 604/891.1 |
| 4,716,448 A * | 12/1987 | Kelly | ............. | 257/253 |
| 4,721,601 A * | 1/1988 | Wrighton et al. | ............. | 422/82.03 |
| 4,816,118 A * | 3/1989 | Oyama et al. | ............. | 204/418 |
| 4,968,400 A * | 11/1990 | Shimomura et al. | ............. | 257/253 |
| 5,198,493 A * | 3/1993 | Holmberg et al. | ............. | 525/54.1 |
| 5,506,420 A * | 4/1996 | Kossovsky et al. | ............. | 257/40 |
| 5,874,046 A | 2/1999 | Megerle | ............. | 422/68.1 |
| 5,942,388 A * | 8/1999 | Willner et al. | ............. | 435/6 |
| 5,945,286 A * | 8/1999 | Krihak et al. | ............. | 435/6 |
| 5,965,452 A * | 10/1999 | Kovacs | ............. | 436/149 |
| 5,968,745 A * | 10/1999 | Thorp et al. | ............. | 435/6 |
| 6,150,106 A * | 11/2000 | Martin et al. | ............. | 435/6 |
| 6,290,839 B1 * | 9/2001 | Kayyem et al. | ............. | 205/777.5 |
| 6,391,558 B1 | 5/2002 | Henkens et al. | ............. | 435/6 |
| 6,391,624 B1 | 5/2002 | Megerle | ............. | 435/287.2 |
| 6,541,617 B1 * | 4/2003 | Bamdad et al. | ............. | 536/23.1 |
| 7,129,554 B2 * | 10/2006 | Lieber et al. | ............. | 257/414 |
| 2003/0073071 A1 | 4/2003 | Fritz et al. | ............. | 435/4 |

OTHER PUBLICATIONS

Bott, Electrochemistry of Semiconductors, 1998, Current Separations, 17(3), 87-91.*

Robert M Umek et al., "Electronic Detection of Nucleic Acids, A Versatile Platform for Molecular Diagnostics", Journal of Molecular Diagnostics, vol. 3, No. 2, May 2001, pp. 74-84.

(Continued)

*Primary Examiner*—N. Yang
(74) *Attorney, Agent, or Firm*—Haverstock & Owens LLP

(57) ABSTRACT

A high sensitive detector detects and determines the presence of a very small amount of biological substances. The high sensitive detector comprises a sensor part, a sense amplifier, and microprocessor. A sensor part of the detector comprises two components; one comprises transistors and the other comprises affinity binding molecules for capturing biological substances. The affinity binding molecules can capture biological substances through specific molecular recognition. The electrical properties of a transistor-based circuit are changed when the affinity binding molecules capture biological substances on the gate of the transistors. The electrical signal is amplified by an amplifier and transferred to a microprocessor. The microprocessor modulates the transferred signal to determine the presence of biological substances.

38 Claims, 2 Drawing Sheets

OTHER PUBLICATIONS

Jen-Jr Gau et al., "A MEMS based amperometric detector for *E. Coli* bacteria using self-assembled monolayers", Biosensors & Bioelectronics 16 (2001), pp. 745-755.

Lana Feng et al., "Electronic microarray for DNA analysis", Gene Therapy and Molecular Biology, vol. 4, Dec. 1999, pp. 183-191.

"Lab-On-A-Chip Technology", Core Technology, pp. 1-4.

P. Caillat et al., "Biochips on CMOS: an active matrix address array for DNA analysis", Sensors and Actuators B: Chemical, vol. 61, Issues 1-3, Dec. 14, 1999, pp. 1-9.

Emily A. Smith et al., "Formation, Spectroscopic Characterization and Application of Sulfhydryl-Terminated Alkanethiol Monolayers for the Chemical Attachment of DNA onto Gold Surfaces", Langmuir, vol. 17, No. 8, Apr. 17, 2001, pp. 2502-2507.

Danny Porath et al., "Direct Measurement of Electrical Transport Through DNA Molecules", Nature, vol. 403, Feb. 10, 2000, pp. 635-638.

Hans-Werner Fink et al., "Electrical Conduction Through DNA Molecules", Nature, vol. 398, Apr. 1, 1999, p. 407.

* cited by examiner

DIRECT ELECTRIC BIOLOGICAL AGENT DETECTOR

CROSS-REFERENCE TO RELATED APPLICATIONS

This application claims the benefits of provisional U.S. Patent Application Ser. No. 60/382,401 filed on May 20, 2002, the disclosure of which is hereby incorporated herein by reference in its entirety.

FIELD OF THE INVENTION

This invention relates to a device for detecting biological substances such as virus, bacteria and other cells. A primary object of the present invention is to provide a device for detecting an extremely small amount of biological substances at nearly real time. A further object of the present invention is to provide a device for detecting various kinds of biological substances. The present invention is particularly useful to detect biological infection at the early stage and to make a quick and effective response to prevent outbreaks of the infection for national defense.

BACKGROUND OF THE INVENTION

The development of rapid, accurate diagnosis methods for the detection of pathogen microbes and disease signature bio-molecules are longstanding goals of medical scientific researchers. After Sep. 11, 2001, this has become a high priority biodefense requirement in national defense. Various techniques have been developed in an attempt to achieve this goal.

Current technologies of detecting biological substances include a cell culture method, an immune assay method, and a gene amplification method. These technologies have limitations because of unacceptable chances of false positives and the further requirements of expensive equipment, highly skilled users and long detection time.

A cell culture method typically detects bacteria by culturing bacteria in liquid media or on the surface of media solidified by agar. The disadvantages of the cell culture method include low sensitivity and detection generally takes an unacceptably long time. Some bacteria and virus strains such as mycoplasma species are difficult to culture because they are intracellular microorganisms. Some microorganisms take an extremely long time to culture. For example, it takes six weeks to culture bacteria causing Lyme's Disease for its detection.

An immune assay method detects infectious agents by observing antibody-antigen reaction. This method has been commonly used in clinical diagnosis. One of the disadvantages of the immune assay method is that there is a cross-reaction in the immune detection. The other disadvantage is unacceptably low sensitivity. Thus, a large amount of target agent is required so that this method is not effective to detect a small amount of antigen or molecules such as a few anthrax spores.

A gene amplification method detects a target DNA by a polymerase chain reaction. An advantage of this method is that it can detect a very small amount of a target DNA. It has extremely high sensitivity compared to an immune assay method. A disadvantage of the gene amplification method is that it provides an unacceptable level of false positive observations, which are caused by contamination or mismatch annealing in the gene amplification process. Moreover, this method is expensive in that it requires highly skilled persons and specialized equipment.

Most of the biosensors available today are optical sensors. A few of them have good specificity and sensitivity. However, since these optical sensors require complex techniques, their application is limited. Moreover, these optical sensors require multiple labeling processes done by skilled professionals. Detection by the optical sensors and the data analysis requires specific and expensive instruments.

Electrochemical technologies have been used in the development of bio-sensors for the past 15 years. These technologies allow a near real time detection and relatively lower cost detection instrument compared to optical bio-sensors (see U.S. Pat. No. 6,391,624 to Megerle, U.S. Pat. No. 5,942,388 To Willner, et al. and U.S. Pat. No. 4,585,652 to Miller, et al). However, these methods depend on oxidation and reduction reaction in the detection process. In most cases, target agents or the capture molecules, (ie. probes,) need to be modified or labeled with redox elements, in order to create such a reaction. It is a complicated chemical process.

Therefore, simple detection processes and low cost devices need be developed. Recently, semiconductor technologies that produce computer chips are considered and used with biotechnology in the development of bio-sensor devices. This invention focuses on a mechanism, which reports biological interaction events as electronic signals.

SUMMARY OF THE INVENTION

A high sensitivity detector detects and determines the presence of a very small amount of target biological substances (i.e. target agents). The high sensitivity detector comprises a sensor part, a sense amplifier, and a control system such as a microprocessor. The sensor part of the detector comprises two components; transistors and affinity binding molecules for capturing target agents. Affinity binding molecules, immobilized on the detection surface can capture and bind to the target agents through molecular recognition.

To improve specificity and accuracy, small organic molecules are used as spacer molecules to prevent nonspecific binding and prevent direct contact of ionic molecules in solution with the detection surface. This will reduce false positive signals.

The key element in this invention is the signal molecule that reports a biological event as an electronic signal. A signal molecule comprises two parts, a head and a tail. The head is a molecular recognition element that is specified by its affinity binding molecules. The head competes with the target agents in binding to affinity binding molecules. The interaction of heads to affinity binding molecules is reduced when target agents are captured on the detection surface. The tail is a charged molecule that brings electrical charge to the detection surface. The tail can be linked to different heads used in different detection events. It can also be designed to carry positive or negative charge depending on the type of transistor (p-type or n-type) used in the detection electronics.

The electrical properties of the transistor-based circuit are changed when the target agents are captured. Therefore, the electrical signal generated in the circuit is changed. The electrical signal is amplified by an amplifier and transferred to the control system. The control system modulates the transferred signal to determine the presence of biological substances.

The present invention describes the means to generate detectable electronic signals which represent the recognition of biological agents, whereby, specific bio-molecular interaction events can be identified with electronics. Moreover, a universal signal generation process is designed to address the complexity of bio-molecular interactions.

The electronic devices of the invention are able to detect charge presented to the sensor part, which result from biomolecular interactions on the detection surface. The electronic detection means couple directly or indirectly to a detector surface where signal molecules deposit or fail to deposit charge. The invention can be applied to the detection of a wide region of biological agents, such as virus, bacteria, and cells or other biological agents. In general, the methods of invention for detection of biological agents on electronic devices can be extended to other field-effect sensing devices, such as silicon nanowires.

The apparatus comprises at least the following elements:

A detection surface coated with affinity binding molecules;

Immobilized Affinity binding molecules recognize and capture target agents and signal molecules. The recognition is specific in every case.

Spacer molecules are linked to the detection surface and are small organic molecules which prevents non-specific binding on the detection surface.

Signal molecules comprise two parts: the competitive head which recognize and interact with affinity binding molecules, and a signal tail which possess electronic charge.

A control system is provided which is capable of recognizing the presence of electronic charge induced on the detection surface which result from molecular interaction.

Affinity binding molecules on the surface recognize and interact with target agents and signal molecules. Every affinity binding molecule will bind to a signal molecule or to a target agent. If there are no target agents captured on the detection surface, only signal molecules will bind to affinity binding molecules. The associated electronic charge of the signal molecule is presented to the detection surface. The induced charge is detected in the associated electronics. Target agents captured by affinity binding molecules on the detection surface will result in a reduction of possible interactions between signal molecules and affinity binding molecules, thereby reducing the total charge on the detection surface relative to the case where there are no target agents present. Such a difference is detectable to the detection circuitry.

The electronic devices can be manufactured in most commercial semiconductor fabrication facilities using well-established manufacturing processes producing low cost devices. Such device can be disposable to avoid cross contamination in the detection process and still be inexpensive relative to many current diagnostics. Moreover, the invention can be employed in micro-fluidic channels to increase molecular interaction.

BRIEF DESCRIPTION OF THE DRAWINGS

This patent describes a direct electronic means to detect biological substances. The principle is directed toward providing biological recognition events as changes of electrical properties on the detection surface coupled to electronics, wherein the detection surface is specifically the gate of a field effect transistor. The advantages of the invention described above may be better understood by referring to the following detailed description, the drawings and the claims appended below. In the drawings, like reference characters refer to the same elements throughout the different views. The drawings are not intended to be to scale. Rather, emphasis is instead generally being placed upon illustrating the principles of the invention.

DETAILED DESCRIPTION OF PREFERRED EMBODIMENTS

Embodiments of the present invention are described below. However, it is expressly noted that the present invention is not limited to these embodiments, but rather the intention is that modifications that are apparent to the person skilled in the art and equivalents thereof are also included.

Figure 1:
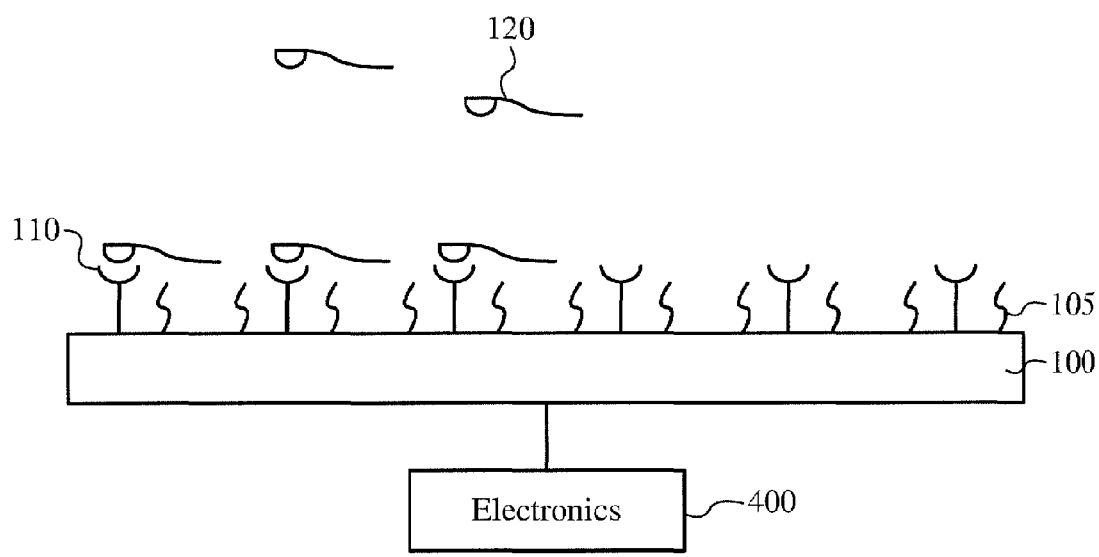
FIG. 1 is a schematic cross-section of the apparatus in the absence of target agents according to an illustrative embodiment of invention

Referring to FIG. 1, a detection surfaces 100 is provided for receiving a biological sample. Preferably, a plurality of detection surfaces 100 are provided and arranged in an array. The detection surfaces 100 are formed on an upper surface of a substrate preferably formed using conventional semiconductor processing techniques. A sample containing area, is provided to surround the array of detection surfaces 100. The sample containing area can be fabricated using any convenient means to define a structure that is suitable for containment of a fluid being tested for having a predetermined biological substance. For example, the sample containing area can be formed of a ring mechanically mounted to the array of detection surfaces, a continuous structure formed of a raised material grown or deposited using conventional semiconductor processing techniques, such as a field oxide, or a package for a semiconductor device with no lid provided such that a fluid sample is maintained in contact with the array of detection surfaces 100. The array of detection surfaces 100 are coupled to electronic circuits 400 described in detail in the discussion of FIG. 3.

A molecular monolayer on the detection surface includes spacer molecules 105, affinity binding molecules 110. In the preferred embodiment, these molecules are covalently linked to the detection surface 100. The linking to the detection surface 100 can be made using any conventional means and can be formed either directly or indirectly.

The spacer molecules 105 are linked to the detection surface and are small organic molecules to prevent non-specific binding and prevent direct contact of ionic molecules in the solution with the detection surface. The spacer molecules are formed of materials such as polyethylene glycol.

Affinity binding molecules are linked to the detection surface to recognize and capture target agents or signal molecules. The affinity binding molecules recognize and interact with specific targets. Affinity binding molecules can exist naturally in biological systems wherein an antibody interacts with an antigen, a ligand interacts with a receptor and an enzyme interacts with a substrate. Affinity binding molecules can also be generated by chemical means wherein phenylboronic acid interacts with salicylhydroxamic acid. Affinity binding molecules can also be generated through molecular evolution process. Other examples of affinity binding molecules are oligonucleotide, polypeptide or other bio-molecules.

The spacer molecules are formed of small organic molecules or organic polymers. Spacer molecules are well known and comprise any of a variety of commercially available organic chemicals. Likewise, spacer molecules can be synthesized and/or modified in the lab. The spacer molecules fill up the surface space to prevent ions and charge in the test sample from directly attaching to the detection surface. Spacer molecules also prevent non-specific binding of non-targets.

The signal molecules 120 comprise a head configured for recognition and interaction with the affinity binding molecule 110 and a tail that is designed to affect the characteristics of operation of the system. The head can be formed of naturally occurring or chemically synthesized parts. The tail is selectively formed of a nucleic acid, peptide or other organic polymer. The tail can be formed of naturally occurring or chemically synthesized parts. The tail is a charged molecule.

Figure 2:
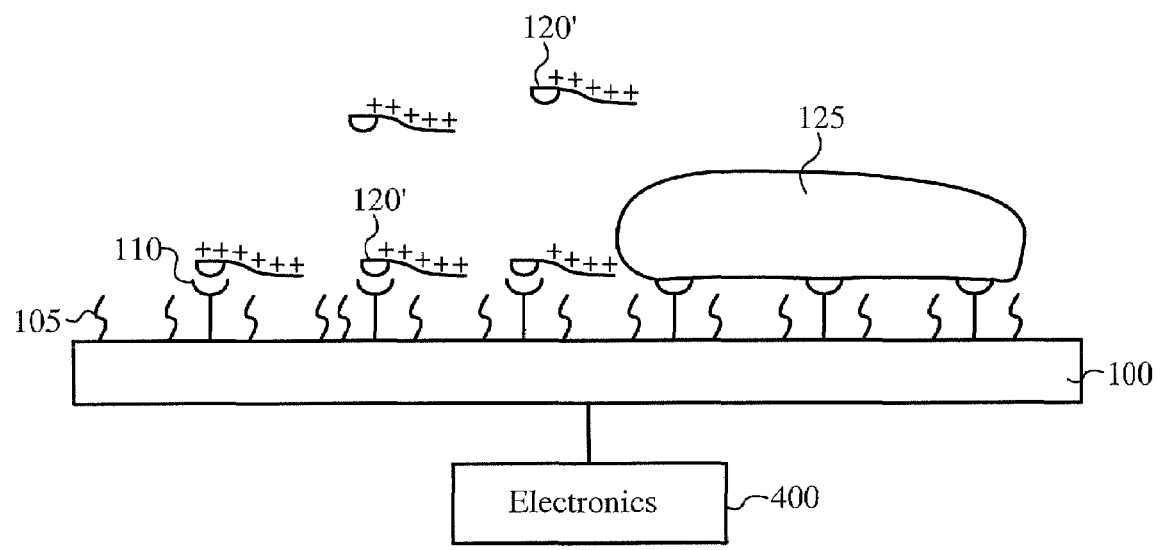
FIG. 2 is a schematic cross-section diagram depicting detection of biological agents, such as bacteria, at a detection surface using charged signal molecules, according to an illustrative embodiment of the invention.

Referring to FIG. 2, spacer molecule 105, together with affinity binding molecules 110, form a molecular monolayer on the detection surface 100. Affinity binding molecules 110 are chosen based on their affinity for a given target agent 125. Charged signal molecules 120', with positively charged tail 120', are bound to affinity binding molecules 110, resulting in a charged surface. The presence of target biological agents 125 reduces the number of signal molecules which can bind to the surface 100 by blocking the binding sites to affinity binding molecules 110.

Figure 3:
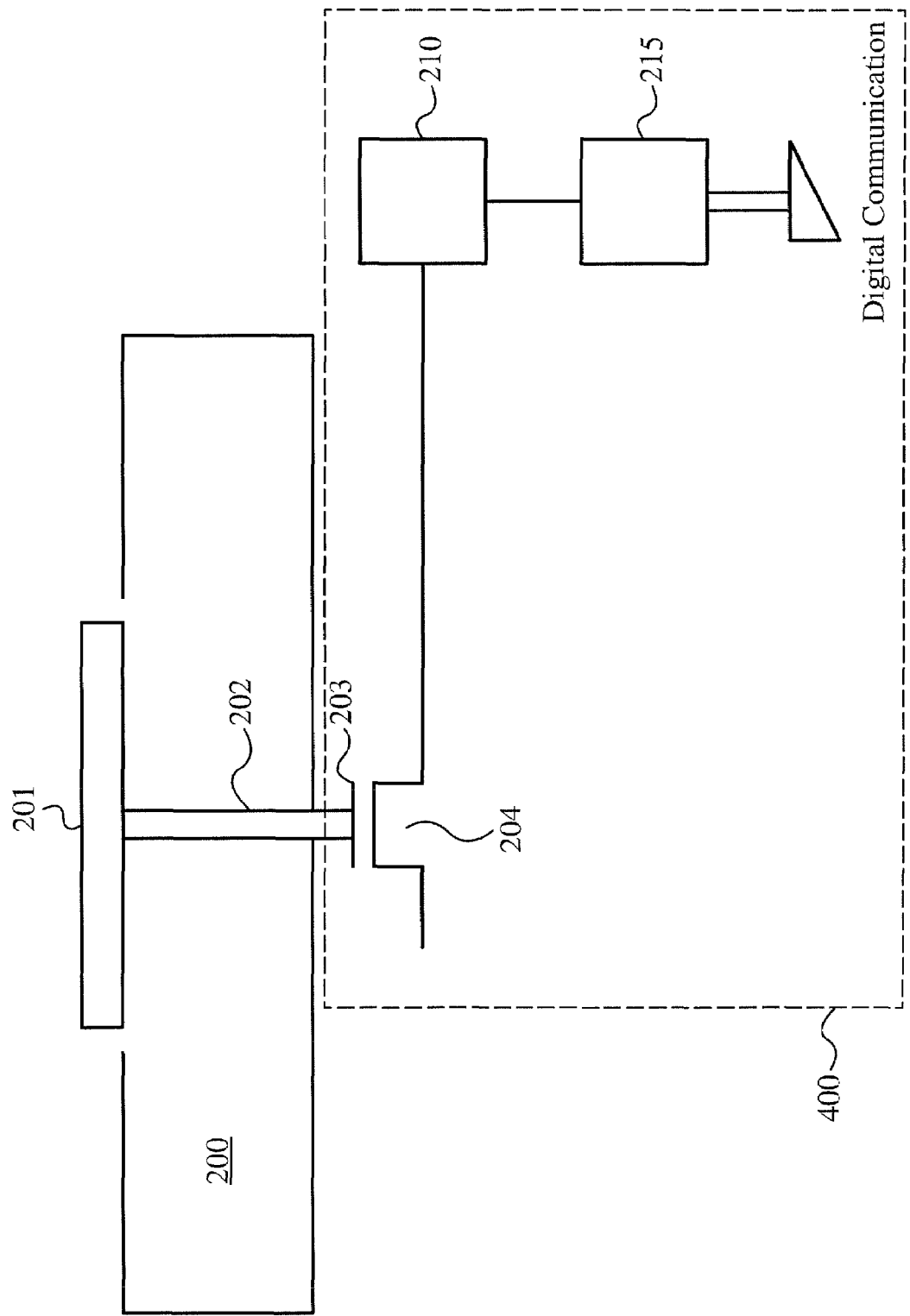
FIG. 3 is a schematic depiction of the electronics which provide a signal path for charge to propagate from detector surface, through a region of metal(s) and arrive at the gate of a field effect transistor the output of which drives amplification electronics and digital analysis circuitry for output on some digital communication channel.

Referring to FIG. 3, the elements of the preferred embodiment include:

1. A detector surface 201. The detector surface 201 is formed of a conductive metal, preferably gold, using any conventional method upon an insulator 200. Preferably, the insulator 200 is formed of silicon dioxide.
2. A conductor path 202 is formed between the detector surface 201 and the electronic circuits 400. The conductor path 202 is preferably formed of metal, including aluminum, other elements commonly used in semiconductor manufacturing processes, or a combination thereof. Alternatively, the conductor path can be formed of a low impedance material such as highly doped polysilicon. The conductor path 202 terminates on a polysilicon gate 203 of a FET transistor 204. Charge is transferred to the affinity binding molecules 110 from the combination of signal molecules 120 and target biological agents 125. It will be understood that the ratio of signal molecules 120 to target biological agents 125 will be proportional to the charge applied to the gate 203 of the FET transistor 204. Naturally, the ratio of signal molecules 120 to target biological agents 125 is directly affected by the presence or absence of target biological agents 125 in the fluid sample. As is well known, the amount of charge transferred to the gate 203 will affect the conductivity of the FET transistor 204 is well known ways.
3. The FET transistor 204 can comprise conventional PMOS, NMOS transistors but is preferably conventional CMOS transistors to limit the power consumed by the system.
4. Amplifier electronics 210 is used to sense the charge transferred to the gate 203 from the combination of signal molecules 120 and target biological agents 125.
5. Digital analysis circuitry 215 is coupled to receive signals from the amplifier electronics 210 to perform accounting, ratio, summation, threshold and other operations appropriate for analysis. In addition, this digital analysis circuitry 210 is configured to drive would drive a digital communication network for providing the result of the analysis to an operator. In the preferred embodiment, the digital analysis circuitry 210 is a microprocessor.
6. The final embodiment of all of the above is for the complete apparatus to reside on a single semiconductor substrate to further reduce the cost of producing the system.

What is claimed is:

1. An electronic device for detection of target biological substances, the device comprising:
   a. a detection surface formed on a gate of a substantially planar insulated gate field effect transistor;
   b. a molecular monolayer formed on the detection surface, the molecular monolayer further comprising:
      i. a plurality of affinity binding molecules, which recognize and interact with the target biological substances and signal molecules; and
      ii. a plurality of spacer molecules;
   c. a signal molecule comprising a head and a tail, wherein the head is a competitive element to the target biological substances and wherein the tail carries electric charge and can be linked to different heads; and
   d. an electronic circuit coupled to the insulated gate field effect transistor to determine a presence of target biological substances by sensing a level of charge induced in the detection surface in response to signal molecules attached to the affinity binding molecules without a reference voltage signal coupled to the gate, wherein substantially no electric current flows from a target biological substance coupled to the detection surface into the insulated gate field effect transistor.

2. The apparatus of claim 1 wherein the tail is selected from the group consisting of a nucleic acid, peptide or other organic polymer.

3. The apparatus of claim 1 where detection surface is a metal conductor.

4. The apparatus of claim 1 where the detection surface is a semiconductor material.

5. The apparatus of claim 1 where the affinity binding molecules are directly linked to the detection surface.

6. The apparatus of claim 1 where the affinity binding molecules are indirectly linked to the detection surface.

7. The apparatus of claim 1 where the affinity binding molecules directly interact with target biological substances and signal molecules.

8. The apparatus of claim 1 where the affinity binding molecules indirectly interact with target biological substances and signal molecules.

9. The apparatus of claim 1 where the spacer molecules are small organic molecules.

10. The apparatus of claim 1 where spacer molecules are linked to the detection surface directly.

11. The apparatus of claim 1 where the head of signal molecules is configured to recognize and interact with the affinity binding molecule.

12. The apparatus of claim 11 where the head is a naturally occurring binding molecule selected from the group consisting of a nucleic acid, peptide, biomolecules and organic chemicals, including anti-antibodies, antigens, DNA fragment and peptide-tag.

13. The apparatus of claim 11 where the head is a chemically synthesized binding molecule selected from the group consisting of a nucleic acid, peptide, biomolecules and organic chemicals, including aptamer, biotin, phenyldiboronic acid.

14. The apparatus of claim 1 where the tail is a molecule which is configured to be linked to any head directly.

15. The apparatus of claim 1 where the tail is a molecule which is configured to be linked to any head indirectly.

16. The apparatus of claim 1 where the affinity binding molecule is an antibody.

17. The apparatus of claim 1 where the affinity binding molecule is an antigen.

18. The apparatus of claim 1 where the affinity binding molecule is an enzyme interactive with a substrate.

19. The apparatus of claim 1 where the affinity binding molecule is a nucleic acid.

20. The apparatus of claim 1 where the affinity binding molecule is a protein nucleic acid.

21. The apparatus of claim 1 where the affinity binding molecule is a polypeptide.

22. The apparatus of claim 1 where the affinity binding molecule is a lectin.

23. The apparatus of claim 1 where the affinity binding molecule is a receptor interactive with a ligand.

24. The apparatus of claim 1 where the affinity binding molecule is a ligand interactive with receptor.

25. The apparatus of claim 1 where target agents interact with affinity molecules firstly; signal molecules interact with affinity molecules secondly.

26. The apparatus of claim 1 where the detection surface is connected directly to the insulated gate of the transistor which further drives other electronics to produce qualifying or quantity data.

27. The apparatus of claim 1 where the detection surface is connected indirectly to the insulated gate of the transistor which further drives other electronics to produce qualifying or quantity data.

28. The apparatus of claim 1 where the electronic circuit measures charge of attached of signal molecules on the detection surface.

29. An electronic device for detection of target biological substances, the device comprising:
- a. a detection surface formed on a gate of a substantially planar insulated gate field effect transistor;
- b. a molecular monolayer formed on the detection surface, the molecular monolayer further comprising:
  - i. a plurality of affinity binding molecules, which recognize and interact with the target biological substances and signal molecules; and
  - ii. a plurality of spacer molecules;
- c. a signal molecule comprising a head and a tail, wherein the head is a competitive element to the target biological substances and wherein the tail carries electric charge and can be linked to different heads; and
- d. an electronic circuit coupled to the insulated gate field effect transistor to determine a presence of target biological substances by sensing a level of charge induced in the detection surface in response to signal molecules attached to the affinity binding molecules without providing a reference electrical potential to the detection surface, wherein substantially no electric current flows from a target biological substance coupled to the detection surface into the insulated gate field effect transistor.

30. The apparatus of claim 29 wherein the tail is selected from the group consisting of a nucleic acid, peptide or other organic polymer.

31. The apparatus of claim 29 where detection surface is a metal conductor.

32. The apparatus of claim 29 where the detection surface is a semiconductor material.

33. The apparatus of claim 29 where the affinity binding molecules are directly linked to the detection surface.

34. The apparatus of claim 29 where the affinity binding molecules are indirectly linked to the detection surface.

35. The apparatus of claim 29 where the affinity binding molecules directly interact with target biological substances and signal molecules.

36. The apparatus of claim 29 where the affinity binding molecules indirectly interact with target biological substances and signal molecules.

37. The apparatus of claim 29 where the spacer molecules are small organic molecules.

38. The apparatus of claim 31 wherein the metal conductor comprises gold.

\* \* \* \* \*